(12) United States Patent
Ziegler et al.

(10) Patent No.: US 6,485,406 B1
(45) Date of Patent: Nov. 26, 2002

(54) MEDICAL RADIOACTIVE IODINE-125 MINIATURE RADIATION SOURCES AND METHODS OF PRODUCING SAME

(75) Inventors: Jürgen Ziegler, Berlin (DE); Claudia Müller, Berlin (DE); Gunnar Mann, Berlin (DE); André Hess, Berlin (DE)

(73) Assignee: Eurotope Entwicklungsgesellschaft fur Istopentechnologien mbH (DE)

( * ) Notice: Subject to any disclaimer, the term of this patent is extended or adjusted under 35 U.S.C. 154(b) by 0 days.

(21) Appl. No.: 09/425,158

(22) Filed: Oct. 21, 1999

Related U.S. Application Data
(60) Provisional application No. 60/109,735, filed on Nov. 24, 1998.

(30) Foreign Application Priority Data

Oct. 23, 1998 (DE) .......................................... 198 50 203

(51) Int. Cl.⁷ .............................. A61N 5/00; A61M 36/14; G21F 9/00
(52) U.S. Cl. ............................... 600/8; 424/1.11; 588/11
(58) Field of Search ........................ 600/1–9; 424/1.29; 280/731; 250/792.3; 588/11; 376/314; 264/641

(56) References Cited

U.S. PATENT DOCUMENTS

| | | | |
|---|---|---|---|
| 3,351,049 A | 11/1967 | Lawrence | |
| 4,312,647 A * | 1/1982 | Tsuchiya et al. | 376/314 |
| 4,323,055 A | 4/1982 | Kubiatowicz | 128/1.2 |
| 4,362,659 A * | 12/1982 | Macedo et al. | 588/11 |
| 4,702,228 A | 10/1987 | Russell | 128/1.2 |
| 4,891,165 A | 1/1990 | Suthanthiran | 252/633 |
| 4,946,435 A * | 8/1990 | Suthanthiran et al. | 600/3 |
| 4,994,013 A | 2/1991 | Suthanthiran | 600/8 |
| 5,163,896 A | 11/1992 | Suthanthiran | 600/8 |
| 5,342,283 A | 8/1994 | Good | |
| 5,354,257 A | 10/1994 | Roubin | 600/7 |
| 5,405,165 A | 4/1995 | Koide | 280/731 |
| 5,683,345 A | 11/1997 | Waksman | 600/3 |
| 5,713,828 A | 2/1998 | Coniglione | 600/7 |
| 5,976,067 A * | 11/1999 | Tucker et al. | 600/2 |
| 5,997,463 A * | 12/1999 | Cutrer | 600/8 |
| 6,149,889 A * | 11/2000 | Chin et al. | 264/641 |
| 6,159,143 A * | 12/2000 | Lennox | 600/4 |
| 6,248,056 B1 * | 6/2001 | Persson | 600/1 |

FOREIGN PATENT DOCUMENTS

WO 9719706 6/1997

\* cited by examiner

Primary Examiner—Eric F. Winakur
Assistant Examiner—Nikita R Veniaminov
(74) Attorney, Agent, or Firm—Norris, McLaughlin & Marcus P.A.

(57) ABSTRACT

The present invention relates to new radioactive iodine-125 miniature radiation sources (seeds) comprising a radioactive carrier matrix which consists of a porous and mechanically stable inorganic material, the pores of which contain inorganic insoluble iodide-125, and which is enclosed within a capsule made of a corrosion-resistant and body-compatible material or which is coated with such a material. The iodine seeds according to the present invention further may contain (a) usual X-ray marker(s). Another object of the present invention are methods for manufacturing said novel iodine-125 seeds.

15 Claims, 1 Drawing Sheet

MEDICAL RADIOACTIVE IODINE-125 MINIATURE RADIATION SOURCES AND METHODS OF PRODUCING SAME

This application claims the benefit of provisional application No. 60/109,735 filed Nov. 24, 1998.

BACKGROUND OF THE INVENTION

1. Field of the Invention

The present invention relates to new radioactive iodine-125 miniature radiation sources (seeds) comprising a radioactive carrier matrix which consists of a porous and mechanically stable inorganic material, the pores of which contain inorganic insoluble iodide-125, and which is enclosed within a capsule made of a corrosion-resistent and body-compatible material or which is coated with such a material. The iodine seeds according to the present invention further may contain (a) usual X-ray marker(s). Another object of the present invention are methods for manufacturing said novel iodine-125 seeds.

Radioactive implants are used in tumour therapy in order to minimize surgical intervention into the patient. They may further be used to prevent the emergence of metastases or in post-operative tissue irradiation.

There are three basic types of irradiation therapy:

1. the interstitial therapy in which the radiation sources are implanted into the tissue to be treated;
2. the intracavitary therapy in which the radiation sources are inserted into a cavity of the human body by means of an applicator in order to expose the surrounding tissue to irradiation;
3. the intraluminal therapy in which the radiation sources are inserted into blood vessels by means of a catheter in order to expose the inner wall of the vessel or the surrounding tissue to irradiation.

For a long time, the exposure of tumours to local irradiation by using interstitial implants has been in common practice. Such method of treatment allows very precise dosing and restricting the treatment to a small area, thus minimizing the irradiation influence on healthy tissue.

The radiation energy of the iodine 125 isotope is appropriate for interstitial brachytherapy. Due to the low gamma energy level and the short half-life value of iodine 125, seeds doped with it may remain in the tissue as permanent implants without destroying healthy tissue. Also, there is no risk for medical staff and other persons being in contact with the patient.

The seeds have to be designed so as to allow a fast and simple insertion of the implants into the tissue to be treated. A common insertion technique uses hollow chamber needles to place the desired number of seeds into the tissue and then to retract the needle.

X-ray and ultrasonic techniques are used to identify the seeds in the body and to indicate their position. For this reason, so-called "markers" are integrated into the seeds, or a design is chosen which enables ultrasonic displaying. These markers are made of materials having a high density as for instance gold, silver, platinum, lead or iridium. They may have different shapes and sizes which depend both on the shape and the size of the radioactive carrier and on the requirements of the imaging and may be shaped as e.g. balls, tubes, wires. Further, it is known that the ultrasonic visualisation may be improved by roughening the surfaces, especially the metallic surfaces, for better reflection (etching).

2. Description of the Related Art

The prior art describes a great number of seeds which can be used as radiation sources in brachytherapy, e.g. in the U.S. Pat. No. 5,405,165 (Carden), U.S. Pat. No. 5,354,257 (Roubin), U.S. Pat. No. 5,342,283 (Good), U.S. Pat. No. 4,891,165 (Suthanthiryan), U.S. Pat. No. 4,702,228 (Russel et al.), U.S. Pat. No. 4,323,055 (Kubiatowicz), U.S. Pat. No. 3,351,049 (Lawrence) and WO 97/19706 (Coniglione). Iodine-125 seeds are disclosed in Lawrence, Kubiatowicz, and Suthanthiryan.

The iodine-125 seeds described in U.S. Pat. No. 4,323,055 (Kubiatowicz) contain a radioactive iodine layer on the surface of a matrix, which is in a preferred embodiment a silver rod which functions both as the active support and as the x-ray marker. Such seeds are manufactured, for example, by using a chemical reaction to transform the silver surface of the silver rod to silver chloride. The exchange of the chloride ion is implemented in a gaseous atmosphere so that silver iodide is chemically bound on the surface. Seeds produced in this manner tend to produce an asymmetric radiation field. Furthermore, the radiation is to a high degree self-absorbed by the silver rod. In this case, to ensure the therapeutically necessary amount of radiation more isotope must be added, i.e., in terms of isotope utilization, source production is less efficient and more costly. Further, the abrasion resistance of the silver rod with respect to the radionuclid is not statisfactorily.

Lawrence (U.S. Pat. No. 3,351,049) describes seeds with radioactive iodine-125 dispersed in an organic polymer, e.g. a nylon filament. Due to the high volatility of elemental iodine which is used in this design a mass production of seeds seems to be not possible.

The seeds described by Suthanthiran in U.S. Pat. No. 5,163,896 contain a metallic substrate which is coated with a radioactive-absorbing material comprising poly (amino acids). In U.S. Pat. No. 4,994,013 the seeds also contain a metallic substrate which is coated with carbon or active charcoal. Both designs are based on a coated metallic rod substrate which has similar disadvantages as described above for the silver rods reported by U.S. Pat. No. 4,323,055 (Kubiatowicz). The radiation is to a high degree self-absorbed by the metallic substrate.

SUMMARY OF THE INVENTION

It is an object of the present invention to provide novel iodine-125 miniature radiation sources which meet all requirements of interstitial therapy and do not have the drawbacks described above. It is the object of the present invention to easily and automatically manufacture iodine 125 seeds in large amounts which provide a good imaging in ultrasonics and fluoroscopy, which matrixes do have a good abrasion resistance and a homogenous radiation dose distribution.

This object of the present invention is achieved by radioactive iodine-125 seeds comprising a radioactive carrier matrix which is enclosed in a corrosion-resistent and body-compatible material, which is transparent for the emitted radiation and resistant to said radiation, wherein the carrier matrix consists of a porous and mechanically stable inorganic material, the pores of which contain inorganic insoluble iodide-125. The inorganic carrier matrix may be encapsulated or coated with the corrosion resistant and body-compatible material.

Physiologically tolerable materials which are suited for encapsulation or coating of the radioactive matrices are well known in the art. They may be composed of a resistant human tissue-compatible metal which also has low atomic weight to minimize X-ray shielding such as e.g. titanium or other corrosion-resistent metal alloy such as e.g. stainless steel. Further, they may be composed of a resistent human tissue-compatible metal compound (using reactive nitrogen, oxygen, methane, or carbon monooxide gases during coating to form carbides, nitrides, or carbonitrides of transition metals or other metals) such as titanium carbide, titanium nitride, titanium carbonitride, titanium aluminium nitride, zirconium nitride and hafnium nitride.

BRIEF DESCRIPTION OF THE DRAWINGS

The features of the invention will be better understood from the following description of a most preferred embodiment with reference to the accompanying drawings in which

In FIG. 1 there is shown a sectional view of a seed having a porous inorganic tube 2 the pores of which contain the radioactive iodide. The inorganic tube 2 is surrounded by a capsule 1. The capsule 1 has an outside diameter of less than 1 mm. Inside the hollow space of the tube 2 an X-ray marker 3 is centrally arranged.

FIG. 2 shows the seed in a longitudinal sectional view. The X-ray marker 3 is a wire which extends from one end of the inorganic tube 2 to the other.

Figure 1:
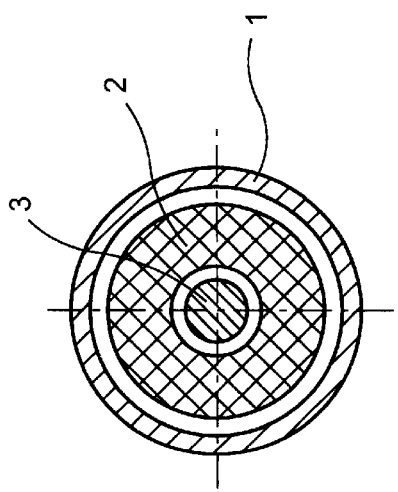
FIG. 1 is a sectional view of a tube-shaped seed in accordance with the invention.
Figure 2:
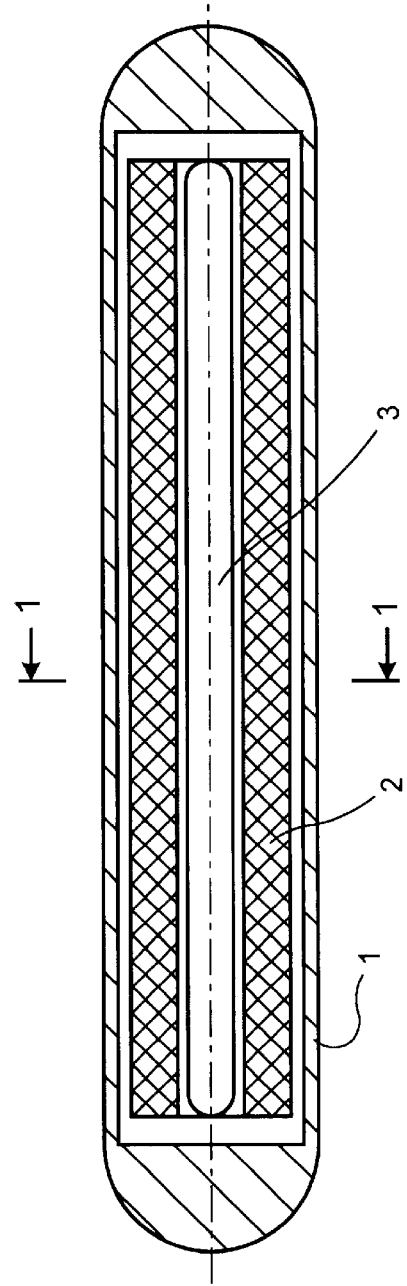
FIG. 2 is a longitudinal sectional view of the seed according to FIG. 1.

The capsule 1 is made of titanium. The two ends of the capsule 1 are laser welded after inserting the inorganic tube 2 including the X-ray marker 3 into the capsule 1.

DESCRIPTION OF THE PREFERRED EMBODIMENT

In a preferred embodiment of the present invention the radioactive matrices are enclosed in a titanium capsule.

In a further embodiment the materials for encapsulation or coating of the matrices may be composed of plastic materials which should be radiation resistant, transparent to the radiation emitted and stable even in very thin layers as e.g. of 2–15 $\mu$m. Such materials are well known in the art and comprise polypropylene, polyethylene terephthalate, nylon, polyurethane, polyphenylene oxide blends, polyphenylsulfone, polysulfone, polyether sulfone, polyphenylene sulfide, phenyletheretherketone, polyetherimide and liquid crystal polymer.

In a preferred embodiment of the present invention Parylene® (poly-p-xylylen) may be used as encapsulation material or coating material.

According to the present invention as carrier matrix designated to carry the radioactive iodine-125 any porous and mechanically stable inorganic material may be used which does not absorb the low-energy gamma radiation of the iodine-125. Preferably inorganic materials which have a porosity of about 15–40% are used, and particularly preferred is a porosity of about 20–30%.

According to the invention the porous inorganic materials of the carrier matrix are selected from the group comprising ceramic materials, insoluble minerals, insoluble salts and inorganic polymers. The ceramic materials, insoluble minerals, insoluble salts and inorganic polymers according to the invention are such materials which cations are selected from alkaline earth metals or their combinations (group 1), from Al, Si, Ga, Sn or their combinations (group 2) or from Ti, Zr, V, Cr, Mn, Fe, Co, Ni, Cu, Zn or their combinations and which anions form oxides, nitrides, carbides, phosphates, fluorides, sulfides or their combinations. It is also possible to use materials which comprise cations of groups 1 and 2, 1 and 3, 2 and 3 or of groups 1, 2 and 3.

Preferably used are for instance clays, porcelain, silicates or mixed metal oxides like zeolithes (Al/Si oxides), perovskites, spinels.

According to the invention especially preferred are ceramic materials, particularly such ceramic materials consisting of $TiO_2$, $Al_2O_3$, $SiO_2$, $ZrO_2$, $Y_2O_3$, mixtures thereof, glas or synthetic glas. It is particularly preferred to use $Al_2O_3$ or its mixtures with said other ceramic materials.

According to the invention the pores of the carrier matrix contain as inorganic insoluble iodide-125 silver iodide, bismuth iodide, lead iodide, thallium-iodide or copper iodide. Particularly preferred silver iodide-125 is used.

Due to the porosity of the inventive inorganic carrier matrix and to the included air the seeds of the present invention already possess a good visibility in ultrasonics. If, additionally, the seed is provided with a X-ray marker (as well known in the art) an extremly good imaging in ultrasonics and fluoroscopy is achieved. According to the invention the materials of the X-ray markers are the common materials used for this purpose. In a preferred embodiment gold is used.

The inorganic matrices of the invention may have any shape which is described in the prior art for radioactive carriers. They may be used in the form of e.g. a rod, hollow tube, film, sheet, microspheroidal particles or pellets. According to the invention the tube-shaped inorganic matrices are preferred. The shape of the X-ray markers, of course, will depend on the shape of the inorganic matrix and on the location of the inorganic matrix within the capsule. The X-ray markers may be placed beside or around the inorganic matrix, or they may be placed centrally within the inorganic material. For example, the X-ray markers may be rotationally symmetrical elements such as rods, tubes, beads, hemispheres or rotationally symmetrical elements having a larger diameter at one or both ends and a lower diamter in the middle (between both ends) of the elements. The X-ray marker may consist of one or more pieces. The marker may occupy the whole or a partial length of the inside of the seed. According to the invention the marker indicates both position as well as orientation of the seeds.

As X-ray markers for tube-shaped inorganic carriers, markers in the form of a wire or tube and arranged centrally in the tube-shaped inorganic carrier are possible in a particularly preferred fashion. As X-ray markers for tube-shaped carriers of an exemplary length of 3.5 mm and an assumed outer diameter of 0.6 mm, wire cuts or tube cuts 0.3–4 mm in length and 0.1–0.7 mm in diameter, as well as beads 0.1–0.7 mm in diameter can be used, for example. Possible forms of markers for this purpose also include other rotationally symmetrical parts having overall lengths of 0.3–4 mm and diameters of 0.1–0.7 mm.

In an especially preferred embodiment of the invention the X-ray marker is used in the form of a wire which is centrally placed within the inorganic matrix.

Preferably, the radioactive inorganic matrix, which is in a preferred embodiment of the invention tube-shaped, and the X-ray marker are inserted into a tube which is closed on one end, and then the other, originally open end of the tube is closed. In the case of a metal tube the second end of the tube is sealed by laser-welding or any other suitable technique such as e.g. electron beam or tungsten inert gas welding.

In the case of a plastic tube the second end of the tube is sealed by gluing, heat sealing, ultrasonic welding or solvent welding.

The radioactive inorganic matrix may also be coated by the plastic material. In this case, the plastic material is molded or shrinked onto the inorganic matrix or the coating is formed by solvent evaporation or polymerisation.

In one embodiment according to the invention the seeds are manufactured by doping the inorganic matrices described above, which are commercially available, with silver chloride, lead chloride, thallium chloride, copper hydroxide or bismuth hydroxide followed by an exchange process to replace the anion with iodide-125. The radioactive inorganic matrices can then be provided with a X-ray marker and encapsulated or coated with a material as described above.

Optionally, the X-ray marker may also be embedded within the inorganic matrix already at the beginning. The presence of the X-ray marker in the interieur of the matrix does not influence the activity loading process.

According to the present invention, different embodiments may be applied to dope the inorganic matrices with the corresponding chloride or hydroxide.

In a first embodiment, a number of inorganic matrices, which e.g. are tube-shaped or rod-shaped, amounting to a maximum of 5,000 units are put into a fine-mesh basket made of platinum fabric or another suitable inert material and immersed in a stirred silver nitrate, lead nitrate, thallium nitrate, copper nitrate or bismuth nitrate solution until they are saturated. The concentration of the respective solution is tuned to the future dose capacity so that the activity range to be utilised is predetermined by this inactive treatment. For example, a silver nitrate solution having a concentration between 60 $\mu$g/ml to 300 $\mu$g/ml is used to provide seeds the activity of which ranges between 0.28 mCi and 0.64 mCi. The overall doping process is performed in a dimmed environment to prevent photolysis. Thereafter, the inorganic matrices are dried at room temperature (RT) or at a maximum temperature of 120° C. and then conveyed into diluted, preferably 0.1N, hydrochloric acid and stirred for a short period. In case of copper or bismuthimpregnated matrices the hydrochloric acid is replaced by 0.1 N sodium hydroxide. Then, the inorganic matrices doped with the corresponding chloride or hydroxide are flushed with distilled water.

In a second embodiment, a number of inorganic matrices, which e.g. are tube-shaped or rod-shaped amounting to a maximum of 5,000 units are put into a fine-mesh basket made of platinum fabric or another suitable inert material and immersed in a silver diamine complex solution ([Ag (NH$_3$)$_2$]Cl) until they are saturated. Thereafter, the fluid adhering to the outer surfaces of the inorganic matrices is removed by means of a gas flow, and the inorganic matrices are dried at a temperature of approx. 80–250° C., preferably 100–150° C. For transforming the silver diamine complex into silver chloride, the inorganic matrices are immersed in diluted hydrochloric acid or an NaCl solution and thereafter flushed with distilled water. The concentration of the silver diamine complex solution has to be chosen this way that the inorganic matrices are doped with 20–40 ng of silver chloride in order to yield the activity ranges of approx. 0.28–0.64 mCi which are usual and necessary for iodine seeds.

The chloride or hydroxide containing inorganic supports obtained by one of the aforementioned embodiments are dried at 80–250° C., preferably 100–150° C., before further processing. The next step is the $^{125}$J exchange which is performed by immersing the matrices in an alkaline Na$^{125}$J solution, preferably a $10^{-4}$ to $10^{-5}$ M NaOH or KOH solution. As a rule, the activity range of the iodine seeds is between 0.28–0.64 mCi which corresponds to a sodium iodide amount of 25 ng to 52 ng per seed. If at least 100 to 5,000 radioactive inorganic matrices are to be manufactured simultaneously, at least 2 ml up to a maximum of 10 ml exchange solution are required. This results in a minimum concentration of Na$^{125}$J of 1.25 $\mu$g/ml ($8\times10^{-6}$ mol/l) and a maximum concentration of Na$^{125}$J of 26 $\mu$g/ml ($1.7\times10^{-4}$ mol/l).

In addition, the exchange solution contains a reduction agent. The molar ratio of reduction agent: Na$^{125}$J amounts to approx. 1:5. According to the present invention, the preferred reduction agents are sodium pyrosulphite (Na$_2$S$_2$O$_2$), sodium sulphite (Na$_2$SO$_3$), sodium thiosulphate (Na$_2$S$_2$O$_3$), or sodium hydrogen phosphate (Na$_2$HPO$_3$). Preferably, the solution is slowly stirred during the exchange reaction. After completion of the exchange reaction, the inorganic matrices are washed to remove the non-exchanged iodine from the inorganic matrices. Thereafter, the inorganic matrices are dried at temperatures between 270 and 400° C., preferably between 300 and 370° C.

In an other embodiment of the invention the seeds may be manufactured in an injection molding or extrusion process by mixing the radioactive iodide with the inorganic material whereas the iodide may arise from an exchange reaction as described above carried out in the same vessel.

In the injection molding process, the flowable inorganic mass, already containing the radionuclide, is forced with pressure into a mold where it solidifies, is removed from the mold, and subsequently tempered. Tempering is used to volatilize or burn out the hydrocarbon-containing plasticizing agent. Depending on the selected matrix, activity carriers of any shape can be obtained by using the injection molding process.

In addition to the injection molding method, an extrusion process may also be used wherein the inorganic mass, already containing the radionuclide, is forced through a die, the strand is collected, tempered in the same way as in the injection molding process, and finally cut to the desired length. Using the extrusion process, tube- or rod-shaped activity carriers can be produced.

According to the invention, the inorganic materials mentioned above are used in the injection molding and extrusion processes, particularly metal oxide powders such as TiO$_2$, Al$_2$O$_3$, SiO$_2$, Y$_2$O$_3$, ZrO$_2$, or mixtures thereof, to which commercially available plasticizing aids are added to adjust the required viscosity and improve the sliding behavior. According to the invention, e.g. cellulose or a cellulose derivative in mixture with a polysaccharide and paraffin are used as plasticizing agent. It is preferred to use microcrystalline cellulose as cellulose. Preferably, 2 parts of cellulose and 3.3 parts of paraffin are used with one part by weight of polysaccharide. The amount of inorganic material depends on the size of the carrier to be produced and is between 200 and 250 mg for the tube-shaped activity carrier preferred according to the invention, the final dimensions of which being a length of about 3.5 mm, an outer diameter of about 0.6 mm, and an inner diameter of 0.22–0.25 mm. The specified components are mixed and, with addition of water, a homogeneous mass is produced. Thereafter, the radionuclide is added in such a way that, for example a solution of AgCl in ammonium hydroxide is pipetted into the sample chamber, followed by addition of a NaI$^{125}$ solution and a reducing agent.

Generally, the formation of the insoluble inorganic iodide-125 is carried out by precipitation within the sample chamber.

Following thorough mixing, the mass is injected or extruded into the prepared mold, to which end machinery with miniaturized sample volumes are to be used as injection molding machines or extruders. The molds for the injection molding process are of such a design that, as a result, activity carriers in the form of tubes, rods, platelets, films, beads, or other molded bodies are obtained.

Injection molding is preferably performed at about 70° C. as low-pressure hot injection molding. The cooled inorganic carriers are then removed from the mold and placed in an oven for tempering.

In extruding, the extruded product is placed on a ceramic backing. In a temperature program wherein the temperature is increased stepwise to at least 300° C., preferably 300–500° C., the parts obtained in injection molding or extruding are subjected to annealing in order to drive out the plasticizing agents as described above.

The X-ray markers can be deposited in the inorganic material before or after injection molding or extruding.

In a preferred embodiment of the invention the X-ray marker is as thin as possible, preferably in the form of a wire, reaching exactly from one end to the other at the inner of the rod or tube or pellet. It is inserted preferably at the end of the manufacturing process. This allows variations with respect to the diameter or the length. In the embodiments according to the present invention, the ultrasonic visualisation is enhanced by the porosity of the inorganic supports. Using fluoroscopy no arte-facts on the screen appear.

According to the present invention, it is possible in the manner described above to manufacture iodine seeds of the sizes and activity levels required in interstitial brachytherapy, wherein the outer diameter, i.e. the diameter of the outer tube encapsulating the radioactive support, should not exceed 0.8 mm.

In a particularly preferred embodiment of the invention the length of the outer encapsulating tube may vary from 1 to 5 mm, the optimal value is about 4.5 mm. The wall thickness may vary from 0.010 mm to 0.150 mm if titanium is used and from 0.002 mm to 0.150 mm if a plastic material is used for encapsulation. The optimal thickness for titanium is about 0.050 mm, for parylene® coating from 10–20 $\mu$m.

The outer diameter of the carrier matrix corresponds to the inner diameter of the encapsulating tube. For a stable manufacturing process (insertion of the matrix into outer tube) the optimal outer diameter of the carrier matrix is 0.100 mm less than the inner diameter of the encapsulating tube.

The length of the x-ray marker may vary from 0.1 mm to the total length of the inner of the tube. The diameter ranges from 0.1 mm to 0.5 mm, whereas the optimal diameter is between 0.15 and 0.25 mm. The optimal length is about 3.5 mm.

The inner diameter of the carrier matrix corresponds to the diameter and shape of the x-ray marker. In case the marker is mechanically inserted into the tube-shaped activity carrier there should be a difference of 0.05 mm in the diameters. It has been found that the iodine-125 inorganic carrier matrices of the invention are characterized by a good abrasion resistance because the radioactive iodine is not present as a layer on a smooth surface but rather, in the pores of the inorganic matrix. The inorganic matrices of the invention are mechanically stable and thus, allow good handling during loading and mounting. Compared with a silver rod as matrix as described in the prior art, the radioactive inorganic matrices according to the present invention exhibit a significantly more homogeneous dose rate distribution and a relatively uniform radiation field around the inorganic matrix is created. The activity range of the seeds of the invention is from about 0.05–5 mCi, preferably about 0.1–3 mCi. The seeds can be manufactured fast and cheaper. According to the exchange method disclosed by the present invention, the radioactive material is used in a controlled manner because, due to the initial inactive chloride or hydroxide doping, the future dose capacity can be determined concretely. Also, the risk of staff contamination is reduced by the inactive chloride or hydroxide doping, and the results of the method can be predetermined more exactly.

Below, the present invention is explained in more detail with embodiments without being restricted thereto.

EXAMPLE 1

Manufacture of 500 Iodine 125 Seeds Having an Activity between 0.422 and 0.457 mCi $Al_2O_3$ ceramic tubes having an outer diameter of 0.60±0.02 mm, a length of 3.5±0.05 mm and an inner diameter of 0.22±0.01 mm are used.

For doping, 839.5 $\mu$g AgCl are dissolved in 100 $\mu$l of concentrated ammonia solution followed by adding distilled water until a volume of 10 ml is reached. The ceramic tubes are then put in a platinum basket and, while stirring, immersed in the aforementioned solution to remain therein for about 5 minutes. Then the basket is taken out of the solution. The ceramic tubes are freed from excess fluid by means of a nitrogen flow of maximum purity and dried for about 10 minutes at 125° C. After having cooled down to room temperature, the tubes are put into the platinum basket again and immersed in 0.05 M HCl in order to completely precipitate the AgCl by destroying the diamine complex. The tubes remain in the stirred solution for 30 minutes. Then the ceramic tubes are washed with distilled water and dried in an oven at 125° C for about 15 minutes.

5 ml of active exchange solution are produced to contain 17.56 $\mu$g $NaJ^{125}$ having a specific activity of 17 Ci/mg and 4.45 $\mu$g $Na_2S_2O_3$ in $10^{-5}$ M NaOH (pH value 8). The cooled ceramic tubes are filled into a tightly lockable glass vessel together with the exchange solution. Said vessel is moved in a rotator for about 1 hour. Thereafter, solution remnants and unexchanged iodine 125 are washed away from the ceramic supports using distilled water. Then, the ceramic tubes are dried for about 15 minutes at 300° C. After cooling down, each tube is provided with a gold wire as marker and inserted into a titanium tube being closed on one end (outer diameter 0.8 mm±0.04, wall thickness 0.05±0.004 mm) which is welded to be sealed in a final step.

EXAMPLE 2

Manufacture of 500 I-125 Seeds According to the Invention, Each having an Activity between 0.422 and 0.457 ml, Using the Injection Molding Process The flowable mass required for the injection molding process is produced as follows: 1100 mg of aluminium oxide having an average grain diameter of 1–5 $\mu$m is placed in a miniature stirred vessel heated to about 70° C., mixed with 60 mg of cellulose powder (microcrystalline cellulose), 30 mg of starch is added, mixed by stirring, and eventually, 100 mg of paraffin is added. Finally, water is added until a coarsely flowable mass of a paraffin-water emulsion is formed which can be transferred without residue into the likewise heated sample chamber of the miniature injection molding machine.

Now a total of 1 ml of a silver diamine chloride solution having an mass equivalent of 840 $\mu$g AgCl is pipetted into the sample chamber, with stirring being effected after each addition. Then, 1 ml of active exchange solution is produced to contain 17.6 μg NaI125 having a specific activity of 17 Ci/mg and 4.45 μg Na$_2$S$_2$O$_3$ in $10^{-5}$ M NaOH. The solution is pipetted into the sample chamber. Following addition of all the aliquots, the remaining volume of water is added util the mass has reached a sufficient plasticity.

Following thorough homogenization, the process of low-pressure hot injection molding is performed at last, wherein the mass is forced into a cold mold where it solidifies, is removed from the mold, and transferred into an oven. Tempering is used to volatilize the hydrocarbon-containing plasticizing agent as well as ammonia to form silver iodide-125 which is homogeneously distributed within the ceramic matrix. In order to carry away reaction gases having formed, the oven is operated in a stream of inert gas. The following temperature program is performed: from room temperature to 300° C. with 5 K/min, then hold at final temperature for 60 minutes and allow to cool.

Eventually, the radioactive ceramic carriers are provided centrally with an X-ray marker and encapsulated in a body-compatible material such as titanium or stainless steel. To this end, the radioactive ceramic carrier including the X-ray marker is preferably introduced in a tube sealed on one end, and the remaining open end is welded using a laser.

The capsule 1 is made of titanium. The two ends of the capsule 1 are laser welded after inserting the inorganic tube 2 including the X-ray marker 3 into the capsule 1.

What is claimed is:

1. A medical radioactive iodine-125 miniature radiation source, comprising a radioactive carrier matrix which emits radiation in a controlled manner, the carrier matrix being formed of a porous and mechanically stable inorganic material chosen from the group consisting of TiO$_2$, Al$_2$O$_3$, ZrO$_2$, Y$_2$O$_3$, and mixtures thereof, the pores of which contain inorganic insoluble iodide-125, which carrier matrix is enclosed in a corrosion-resistant and human body-compatible material, which material is transparent for the radiation emitted from the carrier matrix, and resistant to said radiation.

2. The iodine-125 miniature radiation source according to claim 1, wherein the inorganic material of the carrier matrix has a porosity of 15–40%.

3. The iodine-125 miniature radiation source according to claim 2, wherein the porosity is 20–30%.

4. The iodine-125 miniature radiation source according to claim 1, wherein the pores of the carrier matrix contain as inorganic insoluble iodide-125 at least one chosen from the group consisting of silver iodide, bismuth iodide, lead iodide, thallium iodide and copper iodide.

5. The iodine-125 miniature radiation source according to claim 4, wherein the inorganic insoluble iodide-125 is silver iodide.

6. The iodine-125 miniature radiation source according to claim 1, wherein the material in which the carrier matrix is enclosed is a metal or a metal ally, or a plastic material.

7. The iodine-125 miniature radiation source according to claim 1, wherein the miniature radiation source includes one or more X-ray markers made of high-density metal.

8. The iodine-125 miniature radiation source according to claim 7, wherein the metal is chosen from the group consisting of tantalum, tungsten and gold.

9. The iodine-125 miniature radiation source according to claim 1, wherein the carrier matrix has a form chosen from the group consisting of a tube, rod, film, sheet, and a spherical form.

10. The iodine-125 miniature radiation source according to claim 9, wherein the carrier matrix has a tube form.

11. The iodine-125 miniature radiation source according to claim 1, wherein the X-ray marker is arranged in the carrier matrix or adjacent to the carrier matrix, or surrounds the carrier matrix.

12. The iodine-125 miniature radiation source according to claim 1, wherein the X-ray marker is arranged centrally in the carrier matrix.

13. The iodine-125 miniature radiation source according to claim 1, wherein the X-ray marker is a wire or a tube.

14. The iodine-125 miniature radiation source according to claim 1, wherein a wire or a tube as X-ray marker is centrally arranged in a tube-shaped carrier matrix.

15. The iodine-125 miniature radiation source according to claim 1, wherein the inorganic material is Al$_2$O$_3$.

* * * * *